(12) United States Patent
Liu et al.

(10) Patent No.: US 10,765,270 B2
(45) Date of Patent: Sep. 8, 2020

(54) AUTOMATIC TOOTHPASTE DISPENSING DEVICE FOR PROPER TOOTH CARE

(71) Applicant: HEFEI LONGTOTEM INFORMATION TECHNOLOGY COMPANY LIMITED, High Technology Zone (CN)

(72) Inventors: Guang Liu, Anhui (CN); Yang Li, Anhui (CN)

(73) Assignee: HEFEI LONGTOTEM INFORMATION TECHNOLOGY COMPANY, LTD., Hefei (CN)

( * ) Notice: Subject to any disclaimer, the term of this patent is extended or adjusted under 35 U.S.C. 154(b) by 0 days.

(21) Appl. No.: 16/331,964

(22) PCT Filed: May 8, 2018

(86) PCT No.: PCT/CN2018/085933
§ 371 (c)(1),
(2) Date: Mar. 9, 2019

(87) PCT Pub. No.: WO2018/188673
PCT Pub. Date: Oct. 18, 2018

(65) Prior Publication Data
US 2019/0261818 A1    Aug. 29, 2019

(30) Foreign Application Priority Data
Dec. 12, 2017   (CN) .......................... 2017 1 1321420

(51) Int. Cl.
*A47K 5/18*   (2006.01)
*A61L 2/10*   (2006.01)
*B67D 3/00*   (2006.01)

(52) U.S. Cl.
CPC .................................. *A47K 5/18* (2013.01);
*A61L 2/10* (2013.01); *B67D 3/0003* (2013.01);
*B67D 3/0077* (2013.01); *A61L 2202/11* (2013.01)

(58) Field of Classification Search
CPC ............ A47K 5/18; A61L 2/10; B67D 3/0003
(Continued)

(56) References Cited

U.S. PATENT DOCUMENTS 2,792,856 A * 5/1957 Coppage .................. A47K 5/18
141/362
3,020,941 A * 2/1962 Clifton ..................... A47K 5/18
141/360
(Continued)

FOREIGN PATENT DOCUMENTS

| CN | 201223465 | 4/2009 |
| CN | 101791253 | 8/2010 |

(Continued)

*Primary Examiner* — Vishal Pancholi
(74) *Attorney, Agent, or Firm* — Law Offices of Steven W. Weinrieb

(57) ABSTRACT

Automatic toothpaste dispensing device for due tooth care comprises device holder, which can be divided into a control box, and a toothpaste rack. There are installed a camera, display and a control panel respectively in central, upper and lower part of the said control box. Said toothpaste rack with several toothpaste drums fixed thereon is located to the right side of the control box. Said toothpaste drums include housings, and in the middle of the inner wall of the housings are mounted fixing brackets. On the fixing brackets are installed toothpaste extrusion pumps, above them are toothpaste entrances, and below them toothpaste exits. Below the fixing brackets are installed toothbrush hangers, and on the bottom of inner cavity of the toothbrush hangers squeezing buttons are fixed. The present invention analyzes the teeth
(Continued)

images, estimates teeth conditions, and subsequently obtains an appropriate tooth care plan with the processor.

7 Claims, 2 Drawing Sheets

(58) Field of Classification Search
USPC .................. 222/25, 52, 93, 105, 135, 394
See application file for complete search history.

(56) References Cited

U.S. PATENT DOCUMENTS

| | | | | |
|---|---|---|---|---|
| 4,418,840 A | * | 12/1983 | Gardner, Sr. | B65D 35/285 |
| | | | | 141/360 |
| 5,400,839 A | * | 3/1995 | Cravett | A47K 5/18 |
| | | | | 132/314 |
| 5,487,877 A | * | 1/1996 | Choi | A47K 5/00 |
| | | | | 222/192 |
| 8,393,499 B1 | * | 3/2013 | Sholem | B67D 7/0205 |
| | | | | 222/135 |
| 9,527,716 B2 | * | 12/2016 | Kline | B67D 1/0888 |
| 2007/0157991 A1 | * | 7/2007 | Robertson | A47K 5/1208 |
| | | | | 141/360 |
| 2010/0282773 A1 | * | 11/2010 | Lynn | G08B 21/245 |
| | | | | 222/1 |
| 2013/0292407 A1 | * | 11/2013 | Beavis | B67D 7/221 |
| | | | | 222/1 |
| 2015/0102057 A1 | * | 4/2015 | Gehl | B65D 75/5877 |
| | | | | 222/81 |
| 2015/0173488 A1 | * | 6/2015 | Witchell | G01F 1/42 |
| | | | | 222/23 |

FOREIGN PATENT DOCUMENTS

| | | |
|---|---|---|
| CN | 204463125 | 7/2015 |
| KR | 100760521 | 9/2007 |

* cited by examiner

AUTOMATIC TOOTHPASTE DISPENSING DEVICE FOR PROPER TOOTH CARE

FIELD OF THE INVENTION

The present invention relates generally to household products, and more specifically to an automatic toothpaste dispensing device for due tooth care.

BACKGROUND OF THE INVENTION

Currently automatic toothpaste squeezing devices are commercially available, which take advantage of vacuum, extrusion principle, to have the toothpaste squeezed out automatically after triggering the knob, however, functional property of existing devices is quite low, and compared with squeezing the toothpaste drum with hand, existing device did not save much time. For a long time people have developed teeth brushing habit, and highly value teeth hygiene, till now, tooth care accessories remain indispensable necessities in daily life, tooth care can be so important; out of growing social demands, routine teeth brushing every day cannot meet due tooth care requirements, different tooth care shall be oriented to teeth in different conditions, which demands designing Automatic toothpaste dispensing device for due tooth care.

SUMMARY OF THE INVENTION

The present invention aims to provide automatic toothpaste dispensing device for proper tooth care, to address the problem raised in the previous background segment of this application.

To achieve the above-mentioned effect, the present invention proposes that:

Automatic toothpaste dispensing device for proper tooth care comprises device holder, which can be divided into a control box, and a toothpaste rack. There is installed a camera, display and a control panel respectively in central, upper and lower part of the said control box. Said toothpaste rack with several toothpaste drums fixed thereon is located to the right side of the control box. The toothpaste drums include housings, and in the middle of the inner wall of the housings are mounted fixing brackets. On the fixing brackets are installed toothpaste extrusion pumps, above them are toothpaste entrances, and below them toothpaste exits. Below the fixing brackets are installed toothbrush hangers, on the bottom of inner cavity of the toothbrush hangers squeezing buttons are fixed, and thereunder pressure transducers. There are toothpaste outlets at the lower portion of the outer surface of the said housings, and indicator lights directly above. In the said control box is set a processor, with its input a camera and output a signal activator. Signal receivers, fixed on the toothpaste racks, serve as output of the said signal activator. The said signal receivers will be output via indicator lights, while pressure transducers via the processor. Another output of the processor is the display. A storage device, which is electrically connected with the said processor, is installed in the said control box.

As a further proposal of the present invention: two ultraviolet lamps are installed inside the housing, at the lower part, each located either side of the toothbrush hanger.

As one further proposal of the present invention: a storage battery is installed on the bottom of the control box.

As another further proposal of the present invention: to the back side of the control box and the toothpaste rack are installed suction cups.

Compared to existing techniques, the advantageous benefits of the present invention are:

Prior to tooth brushing, the user shows teeth to the camera, which in turn shoots the teeth, and acquires images of the teeth. Afterwards, the images are imported to the processor, which analyzes it by comparing with image database of teeth in different conditions in the storage device, gets to know the physical conditions of the teeth, as to whether gum inflammation or tooth decay happens, and chooses a corresponding tooth care plan. Different purpose toothpastes have been kept in toothpaste drums on the rack, when the processor sends information to the signal activator and transfers thereby to the signal receiver, a signal will be sent by the receiver to the toothpaste drum that contains the toothpaste suitable for the user to use for that day, and light the indicator thereon, to remind the user to reach the toothbrush to the corresponding toothpaste outlet, and to have it hang on the toothbrush rack. The toothbrush will press the squeezing button downward, as a result, the toothpaste extrusion pump can have the toothpaste extruded, discharged through the toothpaste outlet, and fell on the toothbrush bristles. After feeling pressed, pressure transducer on the bottom will inform the processor, which in turn feedbacks to the signal receiver and turns the indicator light off. Consequently, teeth conditions can be reviewed prior to tooth brushing, and corresponding dental care toothpaste can be used to orient different tooth conditions and keep teeth healthy. Furthermore, when detecting obvious teeth diagnostic symptoms, the processor will automatically connect the Internet of Things, locate drug stores or clinics that have corresponding drugs available, and feedback to the display to have the address and contact of the drug store and drug descriptions shown thereon, to acquaint the user with sufficient information thereof. In addition, the processor will have all teeth conditions images and information stored in the storage device for future reference. Moreover, ultraviolet lamps installed in the lower part of the housing will sterilize the inner space of the toothbrush holders with ultraviolet light, to keep it clean. What's more, suction cups installed to the backside of the control box and toothpaste rack will facilitate to have the device wall-mounted. The processor is connected to the Internet of Things via network signal.

DETAILED DESCRIPTION OF THE ILLUSTRATED EMBODIMENTS

Figure 1:
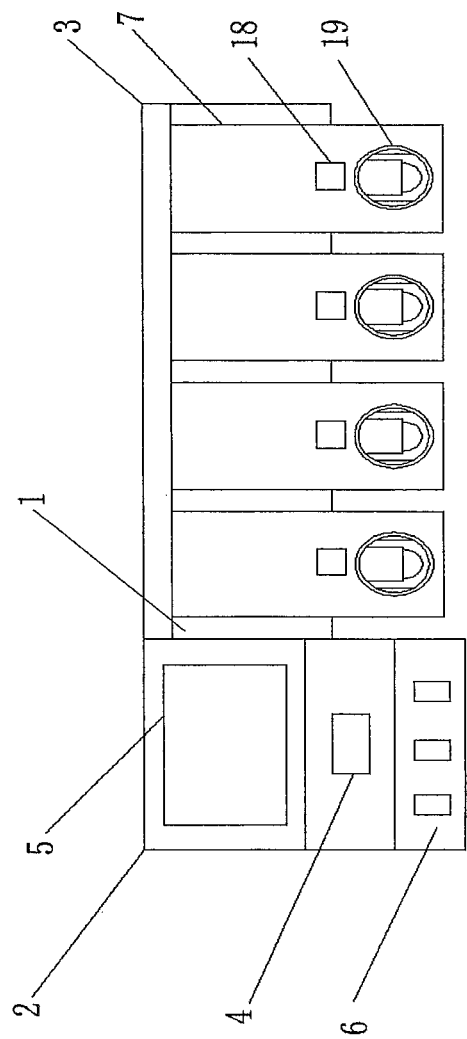
FIG. 1 shows a structural diagram of the present invention.

The list of components noted by reference numbers in the drawings, is as follows:

1—device holder,
2—control box,
3—toothpaste rack,
4—camera,
5—display,
6—control panel,
7—toothpaste drum,
8—housing,
9—bracket,
10—toothpaste entrance, 11—toothpaste extrusion pump,
12—toothpaste exit,
13—toothbrush hanger,
14—squeezing button,
15—pressure transducer,
16—toothpaste,
17—ultraviolet lamp,
18—indicator light,
19—toothpaste outlet,
20—processor,
21—signal activator,
22—signal receiver,
23—Internet of Things,
24—storage device.

In the following paragraphs, in conjunction with the accompanying drawings, a clear and complete description will be given to the technical solutions of embodiments of the present invention, although only some embodiments rather than all are going to be shown here. Based upon the embodiments shown hereinafter, all other variations that those skilled in the art can make without inventive work are included within claimed scope of the present invention.

Figure 2:
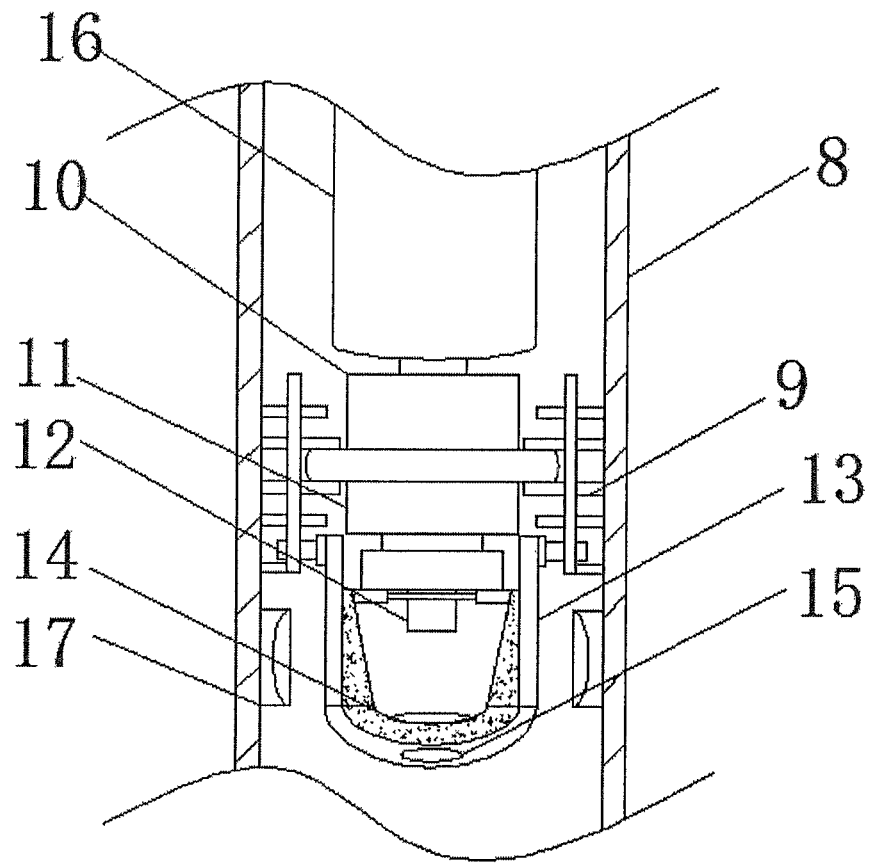
FIG. 2 shows a structural diagram of the toothpaste drum of the present invention.
Figure 3:
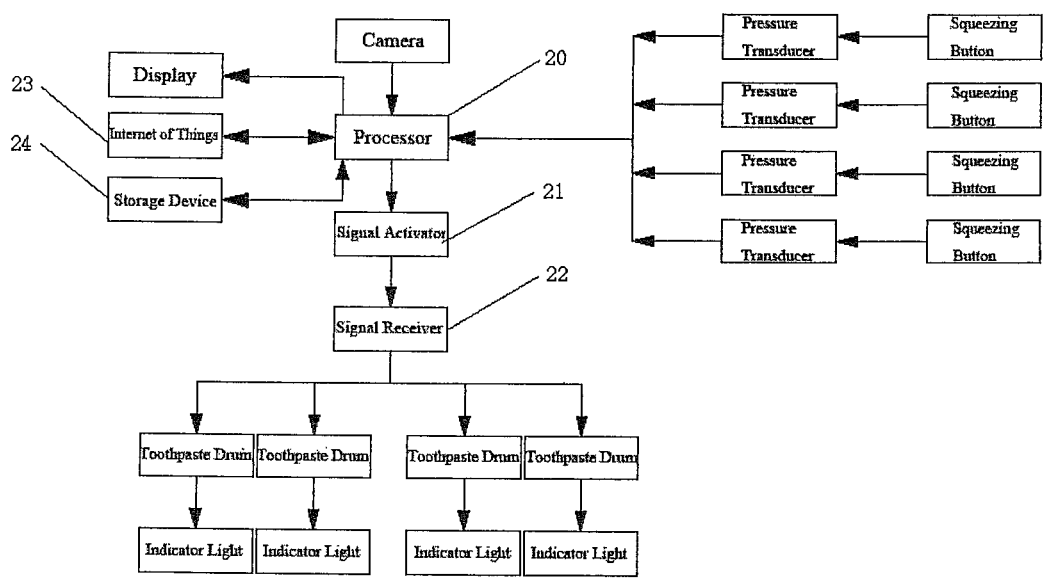
FIG. 3 shows a schematic illustration of the signal connection system of the present invention.

Referring now to FIGS. 1-3, and in accordance with the various embodiments of the invention, an automatic toothpaste dispensing device for proper tooth care comprises device holder 1, which can be divided into a control box 2, and a toothpaste rack 3. There is installed a camera 4, display 5 and a control panel 6 respectively in central, upper and lower part of the said control box 2. The toothpaste rack 3 with several toothpaste drums 7 fixed thereon is located to the right side of the control box 2. The toothpaste drums 7 include housings 8, and in the middle of the inner wall of the housings 8 are mounted fixing brackets 9. On the fixing brackets 9 are installed toothpaste extrusion pumps 11, above them are toothpaste entrances 10, and below them toothpaste exits 12. Below the fixing brackets 9 are installed toothbrush hangers 13, on the bottom of inner cavity of the toothbrush hangers 13 squeezing buttons 14 are fixed, and thereunder pressure transducers 15. Two ultraviolet lamps 17 are installed inside the housing 8, at the lower part, each located either side of the toothbrush hanger 13. There are toothpaste outlets 19, surrounding which is a transparent vinyl cover, at the lower portion of the outer surface of the said housings 8, and indicator lights 18 directly above. In the said control box 2 is set a processor 20, with its input a camera 4 and output a signal activator 21. Signal receivers 22, fixed on the toothpaste racks 3, serve as output of the said signal activator 21. The signal receivers 22 will be output via indicator lights 18, while pressure transducers 15 via the processor 20. Another output of the processor 20 is the display 5. A storage device 24, which is electrically connected with the said processor 20, is installed in the said control box 2. A storage battery is installed on the bottom of the control box 2. Said processor 20 is connected to the Internet of Things via network signal. And to the back side of the control box 2 and the toothpaste rack 3 are installed suction cups.

Compared to existing techniques, the advantageous benefit of the present invention:

Before tooth brushing, facing the control box 2, the user shows teeth to the camera 4, which in turn shoots the teeth, and acquires images of the teeth. Afterwards, the images are imported to the processor 20, which analyzes it by comparing with image database of teeth in different conditions in the storage device, gets to know the physical conditions of the teeth, as to whether gum inflammation or tooth decay happens, and chooses a corresponding tooth care plan. Different purpose toothpastes 16 have been kept in toothpaste drums 7 on the rack 3, when the processor 20 sends information to the signal activator 21 and transfers thereby to the signal receiver 22, a signal will be sent by the receiver 22 to the toothpaste drum 7 that contains the toothpaste 16 suitable for the user to use for that day, and light the indicator 18 thereon, to remind the user to reach the toothbrush to the corresponding toothpaste outlet 19, and to have it hang on the toothbrush hanger 13. The toothbrush will press the squeezing button 14 downward, as a result, the toothpaste extrusion pump 11 can have the toothpaste 16 extruded, discharged through the toothpaste exit 12, and fell on the toothbrush bristles. After feeling pressed, pressure transducer 15 on the bottom will inform the processor 20, which in turn feedbacks to the signal receiver 22 and turns the Indicator light 18 off. Consequently, teeth conditions can be reviewed prior to tooth brushing, and corresponding dental care toothpaste 16 can be used to orient different tooth conditions and keep teeth healthy. Furthermore, when detecting obvious teeth diagnostic symptoms, the processor 20 will automatically connect the Internet of Things 23, locate drug stores or clinics that have corresponding drugs available, and feedback to the display 5 to have the address and contact of the drug store, and drug descriptions shown thereon, to acquaint the user with sufficient information thereof. In addition, the processor 20 will have all teeth conditions images and information stored in the storage device 24, for future reference. Moreover, ultraviolet lamps 17 installed in the lower part of the toothpaste drum 7 will sterilize the inner space of the toothbrush hangers 13 with ultraviolet light 17, to keep it clean. What's more, suction cups installed to the backside of the control box 2 and toothpaste rack 3 will facilitate to have the device wall-mounted.

It is apparent to one of ordinary skill in the art that the present invention is not restricted to the details disclosed in the foregoing exemplary embodiments, in addition, other embodiments can be made without departing from the spirit and technical features of the present invention. Consequently, the described embodiments shall be regarded as illustrative, rather than restrictive, and what is desired protection is defined in the appended claims, instead of the above description, henceforth, all variations that fall into the scope of the equivalents of the claims shall be encompassed in the present invention. None of the nomenclatures of the drawings in the claims shall be taken as limiting the concerned claim.

Moreover, it is to be understood that although description of the present invention is given in terms of embodiments, not every embodiment includes only a single technical solution. Narration of the description is merely for the sake of clarity, those skilled in the art shall consider it as a whole. The technical solutions in the embodiments can also be combined as appropriate to form other embodiments that can be understood by those skilled in the art.

What is claimed is:

1. A method for automatically dispensing toothpaste for proper tooth care, comprising the steps of:
   providing a toothpaste rack upon which a plurality of toothpaste drums, respectively containing different types of toothpaste, are mounted;
   providing a plurality of toothbrush hangers mounted upon said toothpaste rack for respectively mounting a plurality of toothbrushes;
   providing a plurality of dispensing devices respectively operatively associated with said plurality of toothpaste drums for dispensing toothpaste from a particular one of said plurality of toothpaste drums onto a particular one of said toothbrushes when a particular one of said plurality of dispensing devices is actuated;

providing a camera for capturing an image of a person's teeth;

providing a processor having a database within which are stored different images of the person's teeth showing previous conditions of the person's teeth as previously captured by said camera;

using said camera to capture a current image of the person's teeth so as to show a current condition of the person's teeth;

using said processor to compare said current image of the person's teeth, as captured by said camera, with said different images of the person's teeth which are stored within said database and which show said previous conditions of the person's teeth; and using said processor to send a signal to a particular one of said plurality of dispensing devices for dispensing a particular one of said plurality of different types of toothpaste onto a particular one of said plurality of toothbrushes, depending upon said current image captured by said camera showing said current condition of the person's teeth, when compared to said different images of the person's teeth previously stored within said database and showing said previous conditions of the person's teeth, such that said particular one of said plurality of different types of toothpaste, as dispensed onto said particular one of said plurality of toothbrushes, can be used by the user in order to properly address said current condition of the person's teeth.

2. The method for automatically dispensing toothpaste for proper tooth care as set forth in claim 1, further comprising the steps of:

providing a control box for housing said processor; and installing a storage battery within a bottom portion of said control box.

3. The method for automatically dispensing toothpaste for proper tooth care as set forth in claim 1, further comprising the step of:

providing a plurality of indicator lights respectively associated with said plurality of toothbrushes for indicating which particular toothbrush is to be used by the person in order to properly brush the person's teeth.

4. The method for automatically dispensing toothpaste for proper tooth care as set forth in claim 1, further comprising the step of:

providing a plurality of ultraviolet lamps operatively associated with said plurality of toothbrush hangers in order to maintain said plurality of toothbrush hangers clean.

5. The method for automatically dispensing toothpaste for proper tooth care as set forth in claim 2, further comprising the step of:

providing a display panel mounted within said control box for displaying said image of said teeth captured by said camera.

6. The method for automatically dispensing toothpaste for proper tooth care as set forth in claim 1, further comprising the step of:

providing a plurality of transparent vinyl covers are disposed around toothpaste outlets of said plurality of dispensing devices.

7. The method for automatically dispensing toothpaste for proper tooth care as set forth in claim 1, further comprising the step of:

providing a plurality of suction cups mounted upon a rear side of said rack so as to permit said automatic toothpaste dispensing device to be mounted upon a wall.

\* \* \* \* \*